United States Patent [19]

Eisenbeis et al.

[11] Patent Number: 5,464,747
[45] Date of Patent: Nov. 7, 1995

[54] OXIDATION-RESISTANT MUTEINS OF β-GALACTOSIDASE FRAGMENTS

[75] Inventors: Scott J. Eisenbeis, Indianapolis, Ind.; Mark Krevolin, Pinole, Calif.; Christopher P. Bryant, Bourbonnais, Ill.; Sophie J. Boguslawski; David J. Ledden, both of Indianapolis, Ind.; Scott Clark, Berkeley, Calif.

[73] Assignee: Boehringer Mannheim Corporation, Indianapolis, Ind.

[21] Appl. No.: 146,633

[22] Filed: Oct. 29, 1993

[51] Int. Cl.[6] .............................. C12N 9/38; C12N 15/56; G01N 33/535
[52] U.S. Cl. .................. 435/7.6; 435/18; 435/69.1; 435/172.1; 435/188; 435/207; 435/963
[58] Field of Search .................. 435/7.6, 18, 69.1, 435/172.1, 188, 207, 963; 930/240; 935/14

[56] References Cited

U.S. PATENT DOCUMENTS 5,120,653   6/1992   Henderson .................. 435/252.33

Primary Examiner—David Saunders
Attorney, Agent, or Firm—Marilyn L. Amick; Max J. Kenemore; D. Michael Young

[57] ABSTRACT

A mutein of an enzyme acceptor polypeptide fragment of β-galactosidase which is resistant to oxidation is provided. The enzyme acceptor fragment has an amino acid other than cysteine located at position 602 of the natural sequence. An especially preferred substitution is serine. Also provided are a method for producing the novel mutein, a reagent composition comprising the novel mutein, and an immunoassay method for determining an analyte in which the novel mutein recombines with an enzyme donor polypeptide fragment to form enzymatically active β-galactosidase.

16 Claims, 4 Drawing Sheets

OXIDATION-RESISTANT MUTEINS OF β-GALACTOSIDASE FRAGMENTS

BACKGROUND

The present invention relates to modified enzyme acceptor polypeptide fragments of β-galactosidase which are resistant to oxidation, to processes for the preparation thereof, and to the use thereof as reagents in enzyme complementation immunoassays.

A number of homogeneous immunoassays have recently been described that utilize the complementation or reassociation of enzymatically-inactive polypeptide fragments to form active enzymes as a step of generating a detectable signal which can be utilized to determine the amount of an analyte of interest that may be present in a sample such as blood serum. Several of these assays propose utilizing the enzyme β-galactosidase as the enzyme formed by complementation.

Enzyme complementation involves the association of two or more inactive polypeptides which together provide the structural information required for the formation of a biologically active enzyme complex resembling that of the native parent enzyme. The enzymatically-inactive polypeptide fragments can be obtained as the result of proteolysis, chemical cleavage, chemical synthesis, or as the result of a missense or nonsense mutation of the gene coding for the active enzyme. Examples of protein complementation systems which yield an enzymatically-active complex are the ribonuclease-S' complex, the staphylococcal nuclease T complex, various two- and three-fragment complexes derived from cytochrome c, and the alpha- and omega-complementation complexes of *E. coli* β-galactosidase. The interactions which stabilize these complexes are non-covalent in nature and are similar to those involved in the formation and maintenance of the three-dimensional structure of the native enzyme.

Enzyme complementation has been utilized as the underlying basis for the development of a novel homogeneous immunoassay technology. Farina and Golke, U.S. Pat. No. 4,378,428 issued Mar. 29, 1983, and Gonelli et al., (1981, *Biochem. and Biophys. Res. Commun.* 102:917–923) describe an immunoassay based upon the reassociation of S-peptide and S-protein, both of which are derived from the proteolytic cleavage of ribonuclease A, to generate ribonuclease catalytic activity. Specific components of the assay system include an analyte covalently attached to the S-peptide (amino acids 1–20), free S-protein (amino acids 21–124), an antibody specific for the analyte, and a substrate of ribonuclease which is capable of being converted to a reporter molecule. The anti-analyte antibody inhibits the association of the analyte:S-peptide conjugate with the S-protein, thereby reducing the level of enzymatically-active complex and thus the signal generated by the enzymatic reaction. In the presence of a sample containing free analyte, a competition for the antigen binding site occurs between sample-born analyte and the S-peptide conjugate. The concentration of S-peptide conjugate free to participate in complementation with the S-protein fragment, and the resulting signal due to the enzymatic activity of the ribonuclease A' complex, are directly proportional to the concentration of free analyte in the sample.

A similar immunoassay system based on the alpha-complementation system of *E. coli* β-galactosidase polypeptide fragments is described in Henderson, U.S. Pat. No. 4,708,929, issued Nov. 24, 1987, and Henderson, PCT Appl. No. PCT/US90/02491, published Nov. 15, 1990, both of which are herein incorporated by reference. Galactosidase alpha-complementation involves the association of an alpha-acceptor polypeptide fragment and an alpha-donor polypeptide fragment and the subsequent formation of an enzymatically active β-galactosidase molecule. The alpha-acceptor is derived from the internal deletion or chain interruption of consecutive amino acids located within the N-terminus proximal segment of the β-galactosidase molecule. Specific examples include the lac Z M15 β-galactosidase deletion mutant lacking residues 11–41 of the wild-type sequence, and the lac Z M112 mutant in which residues 23–31 have been deleted. The alpha-donor polypeptide can be derived from chemical or proteolytic cleavage of the wild-type protein. The cyanogen bromide fragment CNBr2 composed of amino acid residues 3–92, or the V8 protease peptide spanning residues 3–40, both possess alpha-donor activity.

Alpha-donor and alpha-acceptor polypeptides can also be generated through the application of recombinant DNA technology and peptide synthesis techniques. A readily available supply of these molecules and the ability to modify the structure of either the alpha-donor or the alpha-acceptor polypeptides through these techniques has led to the development of an optimized complementation system which has been employed in cloned enzyme donorbased homogeneous immunoassays. The alpha-donor molecule can be chemically coupled with a specific analyte of interest through the modification of either a cysteine or lysine residue which has been suitably located within the sequence of the alpha-donor molecule such that the conjugation does not interfere with the complementation reaction. Complementation between the alpha-acceptor and alpha-donor can be modulated by an antigen-antibody reaction between an analyte-specific antibody and the alpha-donor to which an analyte has been conjugated. In the presence of free analyte, a competition between the free and alpha-donor-conjugated analyte is established for the antigen binding site of the antibody. Thus, an increase in the level of free analyte results in an elevation in the quantity of alpha-donor conjugate which is available for complementation with alpha-acceptor. As a result, the concentration of the alpha-acceptor:alpha-donor complex and reporter molecule produced from the reconstituted enzymatic activity increase and are proportional to the concentration of the free analyte present in the sample. A dose response curve can be constructed by following the activity, i.e., the slope of the rate of the reaction, at several different concentrations of free analyte. The enzyme activity observed at an infinite concentration of free analyte or in the absence of antibody is defined as the "open rate" and represents the maximal signal obtainable from the assay system.

Krevolin and Kates, European Appl. No. 92304354.1, published Nov. 19, 1992, the content of which is herein incorporated by reference, describe enzyme complementation assays involving complementation in the omega region of β-galactosidase between two polypeptide fragments of the whole β-galactosidase molecule formed by a break in the primary structure of β-galactosidase in the omega region. As in alpha complementation, in some cases the two fragments are not strictly complementary so as to form an exact β-galactosidase amino acid sequence without gaps or overlaps; both gaps and overlaps are possible as long as the resulting fragments can assemble into an active β-galactosidase molecule. Like the alpha-acceptor, the omega-acceptor polypeptide is the larger of the two fragments and normally contains about two-thirds of the amino acid sequence of the natural or modified, full-length β-galactosidase. The omegadonor molecule is the smaller fragment containing the remaining one-third (approximately) of the amino acid sequence; the omegadonor molecule is derived from the C-terminus of the β-galactosidase molecule.

However, the stability of reagent compositions containing these alpha- and omega-acceptor polypeptide fragments of β-galactosidase has been discovered to be less than optimal. There is a gradual and significant loss of activity of the reformed enzyme as storage time of the fragments increases. It is well known that enzymes are unusually susceptible to thermal denaturation and to proteolytic cleavage. Enzymes also contain reactive amino acid side chains located in positions which render them particularly susceptible to chemical modification, including oxidation. In general, it is not possible to predict from the amino acid sequence the extent to which any of the above modifications will occur. Khanna et al., U.S. Pat. No. 4,956,274, issued Sep. 11, 1990 addressed this problem by the addition of an ionic surfactant or a surfactant derived from a sugar residue to the reagent medium containing the peptide fragment. Since the presence of surfactant is generally not compatible with the complementation of the enzyme acceptor and enzyme donor, excess surfactant must be neutralized or removed such as with a cyclodextrin.

The stability of the major constituents which compose the working reagents used in an assay represents an important factor in the overall viability of the assay within the commercial market place. The degradation of any key component of the assay may drastically alter the performance, and thus affect the validity of the results obtained from the assay. Furthermore, if the reagents are unstable, the user may be required to perform laborious and time-consuming tasks such as daily reagent preparation. These repetitive tasks decrease the convenience of the assay to the user. An unstable assay system also limits the shelf-life of the working reagents and thus decreases the number of tests which can be packaged in an assay kit. By increasing the usable number of assays obtainable from a given quantity of reagent, the economic value of the assay kit can be substantially increased.

The most labile components of an enzyme-based immunoassay are normally the protein constituents. The function of a protein, whether it is the catalysis of a chemical reaction or the binding of a specific molecule, is intrinsically dependent upon its discrete three-dimensional structure. It is generally accepted that the three-dimensional structure of a protein is determined by its amino acid sequence. A change in the chemical nature of any particular amino acid within the protein sequence may therefore affect the folding and/or conformation of the folded molecule. Such conformational changes can often lead to a perturbation in the normal function of the protein. The difference between the free energy of the folded and unfolded states of a protein is relatively small, typically only 5–20 kcal/mol. Thus, minor changes in the environment surrounding a protein, e.g., pH, temperature, or ionic strength, can also have dramatic effects on its conformational state. Changes in the conformational state of a protein, particularly to a metastable or partially folded intermediate, can lead to the irreversible aggregation or non-specific adsorption of proteins to surfaces.

A number of degradative processes can occur which alter the chemical properties, and potentially the conformational integrity, of a protein. These include the deamidation of asparagine or glutamine residues to their respective acids; the oxidation of cysteine, methionine, or tryptophan residues to cysteic acid, methionine sulfoxide, or N'-formyl-kynurenine derivatives, respectively; the disruption of disulfide bonds; or the hydrolysis of labile peptide bonds. An understanding of the factors which contribute to the instability of the protein constituents in any given system is a key step in solving protein related stability problems. However, most immunoassay systems involve a number of proteins, and the complexity of their interactions with each other and with other components of the system may limit the number of potential solutions to such problems. In the case of cloned enzyme donor-based immunoassays, the primary protein components include the analyte-specific antibody, enzyme acceptor, enzyme donoranalyte conjugate, and any secondary antibodies which may be necessary for optimization of the assay.

β-Galactosidase is a tetrameric protein having a molecular weight of about 540,000 daltons. The four identical monomers consist of 1023 amino acids, each with a molecular weight of 116,000 daltons. The monomeric protein is divided into three regions: the N-terminus proximal segment (the alpha region), a middle region, and a C-terminus distal segment (the omega region).

*E. coli* β-galactosidase is derived from the Z gene of the lac operon and catalyzes the hydrolysis of β-D-galactopyranosides. The catalytic mechanism of this enzyme involves the general acid catalysis of the glycosidic ester linkage of a substrate molecule by tyrosine-503. This is followed by the loss of the aglycon moiety and the stabilization of a putative carbonium ion intermediate through an interaction with glutamate-461. The final step in the catalytic cycle involves the transgalactosylation of an acceptor molecule, usually water, and the removal of the product from the active site. The active enzyme is composed of four identical subunits with one active site per subunit. Monovalent cations, although not required for activity, dramatically enhance the rate of enzyme catalysis, whereas divalent cations, e.g., $Mg^{2+}$ or $Mn^{2+}$, are required for activity.

The *E. coli* β-galactosidase homotetramer contains 64 cysteine residues (16 cysteine residues per subunit), none of which are involved in either the enzymatic activity or the maintenance of the quaternary structure through intersubunit disulfide bridges, as indicated by the stabilization of the molecule in high concentrations of reducing agents. The efficiency of the in vitro association of individual monomers to form the active tetramer is dramatically increased under conditions in which the cysteines are fully reduced. Similarly, reducing agents greatly enhance enzyme complementation. The alpha-acceptor polypeptide contains all 16 cysteine residues present in a single β-galactosidase subunit. However, alpha-acceptor molecules exist as homodimers in solution. Thus, the surface area normally buried at the dimer-dimer interface in β-galactosidase is exposed in the alpha-acceptor. Chemical modification studies of β-galactosidase with iodoacetate lead to the identification of cysteine-500 and cysteine-1021 as surface accessible residues in β-galactosidase (Jornvall et al., 1978, *Biochem.* 17, 5160–64). Carboxymethylation of these two residues did not affect the activity of the enzyme to any significant extent. However, when M15, a dimeric alphaacceptor molecule, was treated with iodoacetate, three additional cysteine residues at positions 78, 389 and 602 were modified. Carboxymethylation was found to inhibit the ability of M15 to participate in alpha-complementation. This suggests that one or more of these additional residues is situated at the dimer-dimer interface, the modification of which interferes with alpha-complementation.

It was surprising, therefore, to discover that substitution by site-directed mutagenesis of the cysteine-602 residue on an enzyme acceptor polypeptide fragment of β-galactosidase with a conservative amino acid, preferably serine, results in substantially increased stability of the enzyme acceptor mutein over that of an enzyme acceptor polypeptide fragment having cysteine at position 602.

Predetermined, site-directed mutagenesis of tRNA synthetase in which a cysteine residue is converted to serine has been reported (G. Winter et al., 1982, *Nature*, 299, 756–758, and A. Wilkinson et al., 1984, *Nature*, 307, 187–188). Estell et al., U.S. Pat. No. 4,760,025, issued Jul. 26, 1988 describe a cloned subtilisin gene modified at specific sites to cause amino acid substitutions of certain methionine residues. Koths et al., U.S. Pat. No. 4,752,585 issued Jun. 21, 1988 and U.S. Pat. No. 5,116,943, issued May 26, 1992, describe the protection of a therapeutic protein such as interleukin-2 or interferon-β against oxidation by substituting a conservative amino acid for each methionyl residue susceptible to chloramine T or peroxide oxidation.

Buchwalter et al., European Appl. No. 91106224.8, published Nov. 27, 1991, describe an animal somatotropin derivative in which cysteine residues are substituted by site-specific mutagenesis techniques for certain serine and tyrosine residues and in which glutamic acid has been substituted for certain cysteine residues. Breddam et al., PCT/DK91/00103 published Oct. 31, 1991, describe chemically modified detergent enzymes wherein one or more methionines have been mutated into cysteines, and then said cysteines are subsequently chemically modified in order to improve stability of the enzyme toward oxidative agents. Mattes et el., U.S. Pat. No. 4,963,469, issued Oct. 16, 1990, describe a change of an amino acid in the region between amino acid 430 and 550 of β-galactosidase to another amino acid to produce an enzymatically inactive, immunologically active β-galactosidase mutein. Estell et al. (1985, *J. Biol. Chem.* 260, 6518–6521) used site-directed mutagenesis to alter the methionine 222 residue of subtilisin which is a primary site for oxidative inactivation of the enzyme. These authors found that mutants containing non-oxidizable amino acids, i.e., serine, alanine and leucine, were resistant to peroxide inactivation, whereas methionine and cysteine-substituted enzymes were rapidly inactivated.

As used herein, the numbering for the amino acid residues of β-galactosidase will be that published by Kalnins et al., 1983, *EMBO Journal* 2, 593–597, the content of which is herein incorporated by reference. The nucleotide sequence of the lac Z gene coding for β-galactosidase in *E. coli* was determined and β-galactosidase was predicted to consist of 1023 amino acid residues rather than the 1021 residues previously reported by Fowler and Zabin (1977, *Proc. Natl. Acad. Sci. U.S.A.* 74, 1507–1510 and 1978, *J. Biol. Chem.* 253, 5521–5525).

SUMMARY OF THE INVENTION

The present invention provides novel muteins of enzyme acceptor polypeptide fragments of β-galactosidase and processes for producing such muteins. In particular, the present invention provides novel muteins of enzyme acceptor polypeptide fragments of β-galactosidase in which an amino acid other than cysteine is located at position 602. Particularly preferred are alpha-acceptor polypeptide fragments of β-galactosidase in which serine is substituted for cysteine-602. Also provided are reagent compositions comprising these novel muteins and immunoassay methods utilizing such compositions in cloned enzyme donor immunoassays involving complementation between these enzymatically-inactive donor and acceptor fragments to form an enzymatically-active enzyme. The novel enzyme acceptor muteins have been found to exhibit substantially increased stability and resistance to oxidation over that of the parent enzyme acceptor fragment.

The novel muteins of the present invention are conveniently prepared by causing site-directed mutagenesis at the appropriate location on the gene coding for the parent enzyme acceptor. Site-directed mutagenesis methods (Wallace et al., 1981, *Nucleic Acids Res.* 9, 3647–3656; Zoller and Smith, 1982, *Nucleic Acids Res.* 10, 6487–6500; and Deng and Nickoloff, 1992, *Anal. Biochem.* 200, 81–88) permit the replacement of cysteine-602 of β-galactosidase with any amino acid. Chemical synthesis of the polypeptide fragment is not beyond the scope of the present invention; however, such techniques are generally applied to the preparation of polypeptides that are relatively short in amino acid length.

In an assay according to the present invention, an analyte in a sample such as blood serum, i.e., a ligand or receptor, is determined using reagent compositions comprising enzyme donor and enzyme acceptor polypeptide fragments, wherein the enzyme donor fragment is conjugated to an analyte-binding protein specific for the analyte, and wherein the analyte is cross-reactive with the conjugated analyte-binding protein or is complementary thereto. The enzyme acceptor polypeptide consists essentially of a fragment of β-galactosidase which is characterized by forming with the enzyme donor an active enzyme complex having β-galactosidase activity in the absence of analyte-binding protein binding to said conjugate. The reagents are combined with the sample and a substrate capable of reacting with the active enzyme complex in an appropriate assay medium. The rate of conversion of the substrate by the enzyme compared to the rate of conversion of substrate obtained using a known concentration of the analyte is used to determine the amount of analyte in the sample.

BRIEF DESCRIPTION OF THE DRAWINGS

The present invention will be better understood by reference to the following detailed description of the invention when considered in combination with the drawings that form part of the specification, wherein.

DESCRIPTION OF SPECIFIC EMBODIMENTS

In accordance with the present invention, the novel enzyme acceptor polypeptide fragments of β-galactosidase are prepared by site-directed mutagenesis methods, wherein a particular location on the gene coding for an enzyme acceptor fragment is mutagenized. In particular, site-directed mutagenesis methods are used to cause a mutation at the location coding for cysteine at position 602 in the natural sequence, thereby causing the substitution of a conservative amino acid for cysteine. The preferred amino acid substitution is serine. Other amino acids may also be substituted, but conservative substitutions are preferred. By conservative substitution is meant replacement of cysteine-602 of β-galactosidase by an amino acid which has similar characteristics and which is not likely to have an adverse effect on either the enzyme acceptor's ability to complement with enzyme donor or on the catalytic activity of the reformed β-galactosidase. Examples of such conservative amino acid substitutions are glycine, alanine, valine, isoleucine, leucine, serine, threonine and methionine. An especially preferred substitution is serine, and an especially preferred parent enzyme acceptor is EA22, which is described fully in U.S. Pat. No. 4,708,929.

The preparation of parent enzyme acceptors can be accomplished using a variety of recombinant DNA techniques, including deletion constructions or direct synthesis of DNA carrying the desired amino acid sequence followed by in frame ligation into the DNA sequence of the m-region of the lac Z gene which encodes native β-galactosidase. Such techniques are described more fully in U.S. Pat. 4,708,929.

Organisms producing parent enzyme acceptor polypeptide fragments are also publicly available. *E. coli* strain AMA 1004, In Vitro International, Inc. (IVI) (Ann Arbor, Mich.), accession no. 10051, contains a plasmid, pMG22, which carries a gene for a β-galactosidase enzyme acceptor with amino acids 13–40 deleted (EA22). *E. coli* strain AMA 1004, IVI 10050, contains a plasmid, pMG14, which carries a gene for a β-galactosidase enzyme acceptor with amino acids 30–37 deleted (EA14).

As defined herein, an enzyme acceptor is an enzymatically-inactive polypeptide produced by a deletion mutant of the β-galactosidase gene which, when combined with an enzyme donor, is capable of forming enzymatically-active β-galactosidase by the process of complementation. The particular substituted enzyme acceptor muteins described herein are produced from EA22, an enzyme acceptor having a deletion within the alpharegion of the β-galactosidase gene encoding the N-terminus of the β-galactosidase protein. Specifically, EA22 has a deletion of amino acid residues 13–40. Other enzyme acceptor fragments of β-galactosidase which contain the natural sequence which includes amino acid position 602 may also be used to produce muteins according to the present invention. Specific examples of enzyme alpha-acceptors are disclosed in U.S. Pat. No. 4,708,929 and include EA5, EA11, EA14, EA17, EA18, EA20, EA23 and EA24. The distal end of the deletion segment in suitable alpha-acceptors will normally fall between amino acid positions 26 and 54 of the β-galactosidase sequence. In EA22, the distal end of the deletion segment is amino acid 40.

Omega-acceptor fragments are also within the scope of the present invention. Omega-acceptors are fully described in European Appl. 92304354.1, and a specific example of a suitable omega-acceptor is OA721.

The chief consideration when selecting an enzyme acceptor polypeptide of β-galactosidase for stabilization according to the teachings of the present invention is that there has been no previous deletion at position 602.

As defined herein, an enzyme donor is an enzymatically inactive polypeptide comprised of two domains, a donor domain containing a protein sequence capable of combining with an enzyme acceptor to form active enzyme, and an analyte domain capable of interacting with an analyte-binding protein. The analyte domain is either (a) an analyte-coupling domain through which attachment to various analytes or analyte analogs can be accomplished or (b) a protein domain which itself functions as an analyte analog. An especially preferred enzyme donor, ED4, is described in detail in U.S. Pat. 4,708,929.

In the assay method of the present invention, a known amount of an enzyme donor of the β-galactosidase system comprising a coupled or fused analyte (or analogous analyte derivative) of interest, i.e., the enzyme donor conjugate, is combined with a known amount of a specific analyte-binding protein or other binding molecule and a known amount of an enzyme acceptor capable of complementation with the enzyme donor. Competition between the analyte domain of the enzyme donor conjugate and free unknown analyte in the sample for the known amount of specific analyte-binding protein allows the enzyme donor conjugate to remain free so that it binds to the enzyme acceptor. The association of donor conjugates and acceptor results in the formation of a catalytically active enzyme complex, thus modulating the amount of β-galactosidase enzyme activity detectable in the sample. As a result, the amount of free analyte in the sample is determined as a direct function of the measurable enzyme activity. Enzyme activity is measured by monitoring the rate of substrate conversion by the enzyme catalyzed reaction by any of a variety of techniques, including but not limited to spectrophotometric and fluorometric methods.

EXAMPLE 1

Construction of Enzyme Acceptor Mutein

The site-directed mutagenesis of the alpha-acceptor parent, EA22, was carried out according to the method of Deng and Nickoloff, 1992, *Anal. Biochem.* 200:81–88, the content of which is incorporated herein by reference. The starting plasmid which contained the structural gene for EA22 was p230. Two oligonucleotide primers were synthesized which contained twenty uninterrupted bases for hybridization as well as a substitution which introduced the cysteine to serine substitution at position 602. Additionally, the primers incorporated a new restriction endonuclease site and removed a native restriction endonuclease site for screening and selection purposes, respectively.

After the two primers were annealed to the denatured p230, they were elongated with DNA polymerase and transformed via electroporation into a mut S *E. coli* strain defective in strand repair, BMH 71-18. A pool of plasmid obtained from an overnight culture of these cells was transformed again into a lac Z deleted strain, AMA 1004. Plasmids from individual colonies were screened for introduction of a new unique restriction endonuclease site. Positive clones were sequenced for the incorporation of the cysteine-602 to serine change. The final mutagenized product was plasmid p230 with a mutagenized amino acid at the cysteine-602 position as well as two silent changes, one beside the mutagenized amino acid and one at the unique site position elsewhere on the plasmid.

EXAMPLE 2

Comparison of Chemical Instability

In order to determine whether the cysteine-602 to serine substitution had improved the resistance of EA37 to oxidation, an experiment was carried out in which EA22, EA37 and β-galactosidase were exposed to a 1000× molar excess of H$_2$O$_2$. The proteins were exposed to oxidation conditions for variable lengths of time and then assayed for residual β-galactosidase activities.

Assay Buffer

An assay buffer was prepared having the following composition:

150 mM Na phosphate, pH 7.2
400 mM NaCl
4 mM Mg acetate
10 mM ethylene glycol tetraacetic acid (EGTA)
0.05% TWEEN-20 (registered TM of ICI Americas, Inc. for polyoxyethylenesorbitan)
10 mM L-methionine

Measurement of β-galactosidase Activity

Measurement of enzyme acceptor β-galactosidase activity was accomplished by combining enzyme acceptor in assay buffer with alpha-donor ED4 in the presence of the β-galactosidase chromogenic substrate o-nitrophenyl-β-D-galactopyranoside (ONPG). The generation of the rate of the subsequent enzyme activity was then measured spectrophotometrically as a change in absorbance at 420 nm over a fixed length of time. This rate was then compared to the rate obtained for a control sample of fresh or untreated EA22.

Oxidation by Hydrogen Peroxide

Figure 1:
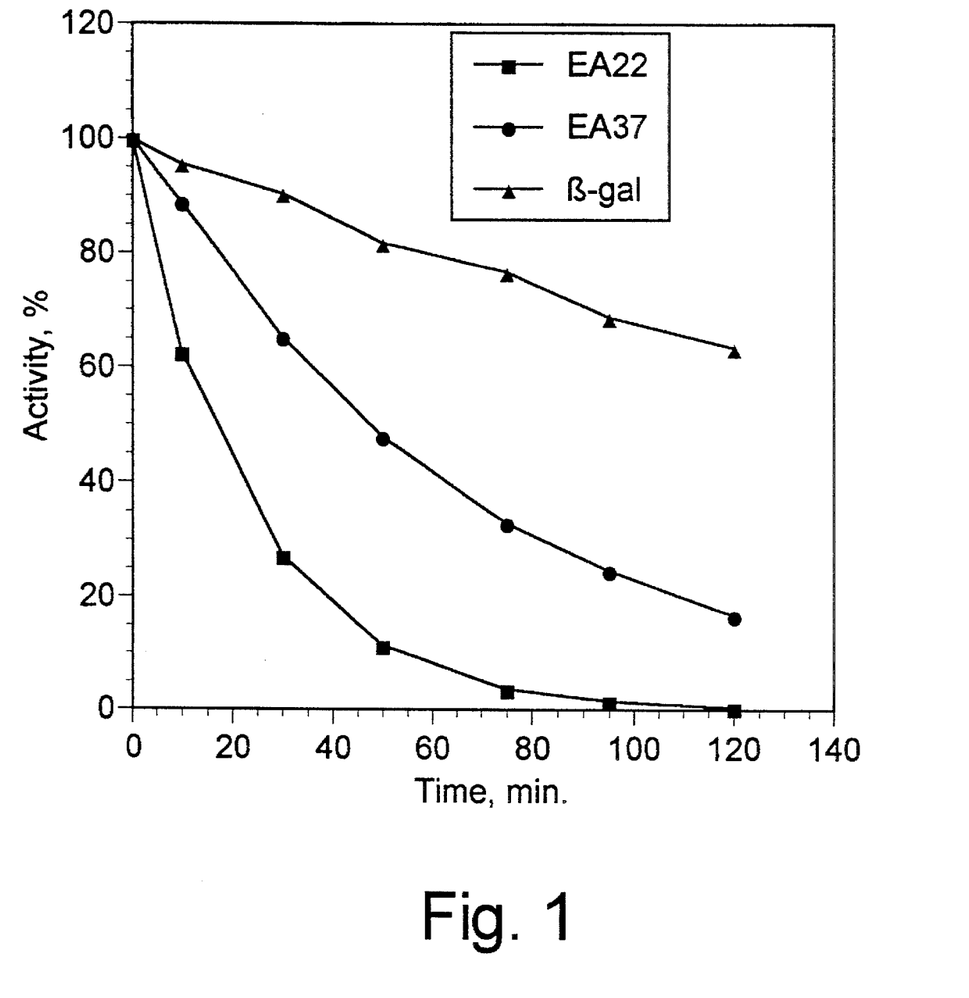
FIG. 1 is a graph showing the loss of enzymatic β-galactosidase activity upon incubation with a buffered reagent containing hydrogen peroxide. The curves represent peroxide inactivation over time for β-galactosidase, EA22 and EA37.

Samples were diluted to a concentration of 4.4 μM in assay buffer containing 4.4 mM hydrogen peroxide. Samples were removed at various time intervals and assayed for residual activity. Inactivation kinetics were found to be first-order in all cases. The loss in kinetic activity for EA22 (k=0.0443 sec$^{-1}$) was found to occur at a rate 11-fold greater than that observed for β-galactosidase (k=0.0038 sec$^{-1}$). In contrast, EA37 (k=0.0149 sec$^{-1}$) exhibited a 3-fold decrease in the rate of inactivation relative to EA22 but were still more susceptible to inactivation than β-galactosidase. The results of these assays are shown in FIG. 1.

EXAMPLE 3

Comparison of Enzymatic Instability

Figure 2:
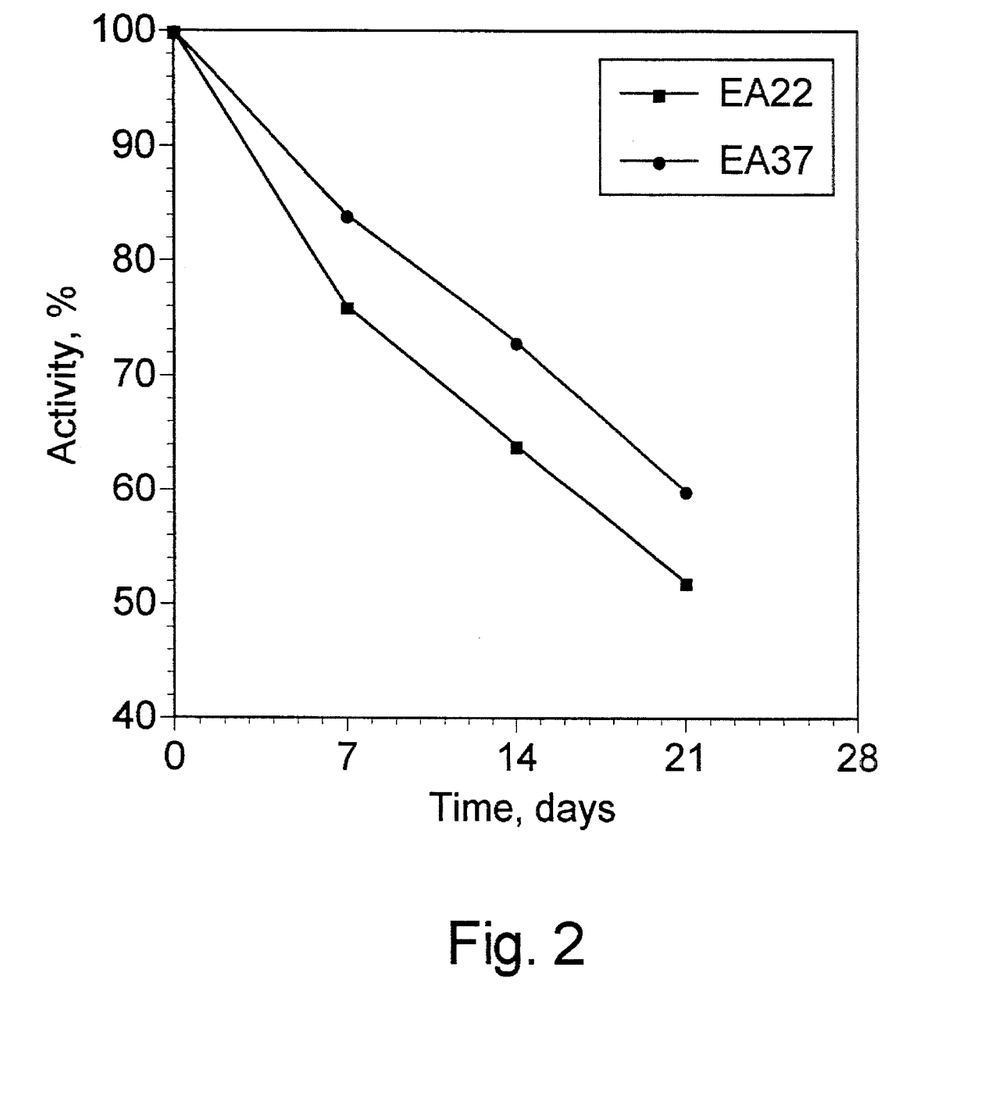
FIG. 2 is a graph showing the loss of enzymatic β-galactosidase activity over time for EA22 and EA37 incubated with buffered reagent.
Figure 3:
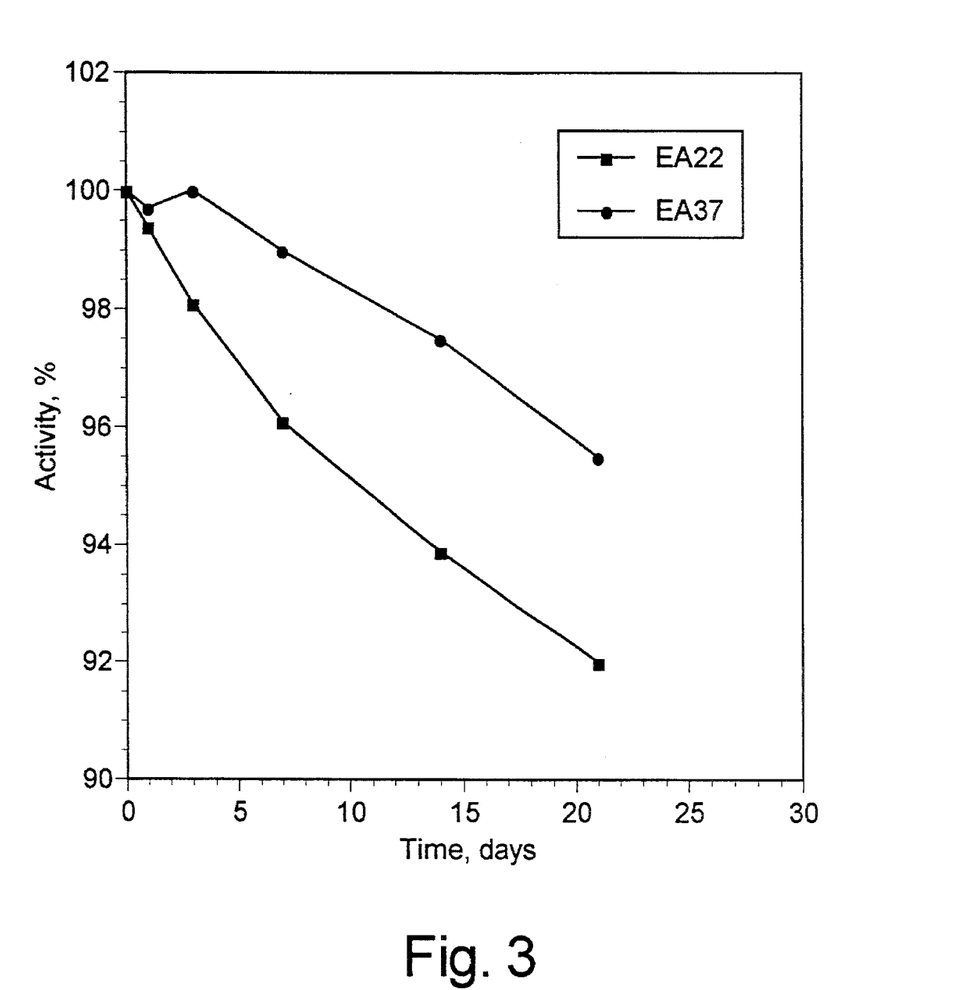
FIG. 3 is a graph showing the loss of enzymatic β-galactosidase activity over time for EA22 and EA37 when incubated with assay reagents for determining barbiturate levels in a specimen sample.

In order to compare the shelf-life stability of the EA22 and EA37 fragments in a liquid, reagents were made comprising each of the fragments in the assay buffer described in Example 2. These reagents were then stored at ambient temperature for various lengths of time and assayed for residual β-galactosidase activity as described in Example 2. The results of these assays are shown in FIG. 2.

EXAMPLE 4

Assay for Barbiturates

Figure 4:
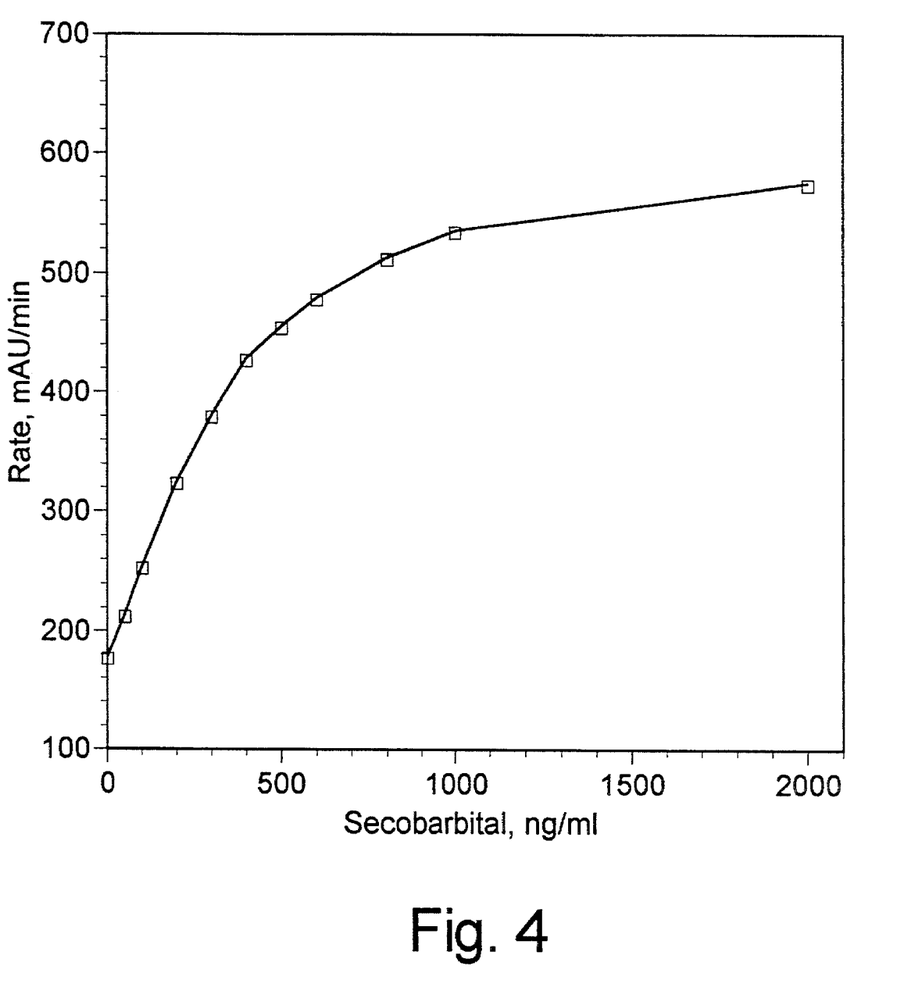
FIG. 4 is a graph showing the rate of substrate conversion by β-galactosidase reformed from acceptor and donor fragments in response to varying levels of analyte.

In order to demonstrate the ability of EA37 to detect an analyte in a sample specimen, varying concentrations of a barbiturate dose (secobarbital) were assayed using a monoclonal antibody specific for barbiturates as the analyte-binding protein, A dose response curve was constructed and is shown in FIG. 4.

EA Reagent 100 mM PIPES (1,4-piperazinediethanesulfonic acid), pH 6.9
700 mM NaCl 10 mM Mg Acetate 10 mM EGTA 20 mM Na Azide
120 U/ml EA37 10 mM L-methionine 0.5% fetal bovine serum
1:800 dilution monoclonal barbiturate antibody (ascites)

ED Reagent 100 mM PIPES, pH 6.9
700 mM NaCl
10 mM EGTA
1 mM EDTA
20 mM Na Azide
2 mg/ml bovine serum albumin fragments
1 mg/ml CPRG (chlorphenylred-β-D-galactopyranoside)
93 mM ED28-barbiturate conjugate

Measurement of Secobarbital

The assay was performed using a Hitachi 717 automated analyzer (Boehringer Mannheim Corp., Indianapolis, Ind.) using equal amounts of ED reagent and EA reagent. The secobarbital dose was added to the EA reagent and incubated for 5 minutes, following which ED reagent was added. The absorbance rate was then measured at 570 nm using a 1-minute read interval at 4'00"–5'00" following the addition of ED reagent. In this particular experiment, the reagent volumes used were 130 μl each and the sample volume was 12 μl. The doses were prepared from an Alltech secobarbital calibrator, 10,000 ng/ml.

What is claimed is:

1. A mutein of an enzyme acceptor polypeptide of β-galactosidase having an amino acid other than cysteine substituted at position 602.

2. The mutein of claim 1, wherein said amino acid is selected from the group consisting of glycine, alanine, valine, isoleucine, leucine, serine, threonine, and methionine.

3. The mutein of claim 1, wherein said amino acid is serine.

4. The mutein of claim 1, wherein said enzyme acceptor polypeptide is an alpha acceptor.

5. A process for producing a mutein of an enzyme acceptor polypeptide of β-galactosidase said mutein having an amino acid other than cysteine substituted at position 602 comprising providing a starting plasmid coding for an enzyme acceptor polypeptide of β-galactosidase, causing a site-directed mutation in the portion of said starting plasmid coding for β-galactosidase amino acid 602 which is normally cysteine, thereby forming a mutagenized plasmid and expressing said mutagenized plasmid to produce said mutein.

6. The process of claim 5, wherein said sitedirected mutagenesis comprises mutagenesis of the portion coding for cysteine at amino acid 602 to code for one selected from the group consisting of glycine, alanine, valine, isoleucine, leucine, serine, threonine, and methionine.

7. The process of claim 5, wherein said site-directed mutagenesis comprises mutagenesis of the portion coding for cysteine at amino acid 602 to code for serine.

8. The process of claim 5, wherein said enzyme acceptor polypeptide is an alpha acceptor.

9. A reagent composition comprising an enzyme acceptor polypeptide of β-galactosidase having an amino acid other than cysteine substituted at position 602.

10. The reagent composition of claim 9, wherein said amino acid is selected from the group consisting of glycine, alanine, valine, isoleucine, leucine, serine, threonine, and methionine.

11. The reagent composition of claim 9, wherein said amino acid is serine.

12. The reagent composition of claim 9, wherein said enzyme acceptor polypeptide is an alpha acceptor.

13. An immunoassay method for determining an analyte in a sample suspected of containing said analyte comprising:

(a) contacting said sample with
   (i) an enzyme donor polypeptide conjugate,
   (ii) an analyte-binding protein specific for said analyte,
   (iii) an enzyme acceptor polypeptide of β-galactosidase wherein said enzyme acceptor polypeptide is characterized by forming with said enzyme donor polypeptide an active enzyme complex having β-galactosidase activity in the absence of analyte-binding protein binding to said conjugate, said enzyme acceptor polypeptide being further characterized by having an amino acid other than cysteine substituted at position 602, and
   (iv) a substrate capable of reacting with said active enzyme complex, such that the rate of conversion of said substrate by said active enzyme complex can be monitored, and wherein said enzyme donor conjugate is capable of competing with said analyte to bind with said analyte-binding protein, thereby inhibiting the formation of active enzyme complex;

(b) measuring the rate of conversion of substrate; and (c) determining the amount of analyte in the sample by comparing the rate of conversion of substrate to a rate of conversion of substrate obtained using a known concentration of the analyte.

14. The method of claim 13, wherein said amino acid is selected from the group consisting of glycine, alanine, valine, isoleucine, leucine, serine, threonine, and methionine.

15. The method of claim 13, wherein said amino acid is serine.

16. The method of claim 13, wherein said enzyme acceptor polypeptide is an alpha acceptor.

* * * * *